(12) United States Patent
Donnelly et al.

(10) Patent No.: US 11,001,267 B2
(45) Date of Patent: May 11, 2021

(54) METHOD AND SYSTEM FOR PROACTIVELY ADJUSTING VEHICLE OCCUPANT BIOMETRIC MONITOR IN VIEW OF UPCOMING ROAD CONDITIONS

(71) Applicant: Lear Corporation, Southfield, MI (US)

(72) Inventors: Patricia Donnelly, Dayton, OH (US); David Gallagher, Sterling Heights, MI (US)

(73) Assignee: Lear Corporation, Southfield, MI (US)

( * ) Notice: Subject to any disclaimer, the term of this patent is extended or adjusted under 35 U.S.C. 154(b) by 55 days.

(21) Appl. No.: 16/529,193

(22) Filed: Aug. 1, 2019

(65) Prior Publication Data

US 2021/0031777 A1 Feb. 4, 2021

(51) Int. Cl.
| | | |
|---|---|---|
| *A61B 1/00* | (2006.01) | |
| *B60W 40/08* | (2012.01) | |
| *B60W 50/00* | (2006.01) | |
| *B60W 40/06* | (2012.01) | |

(52) U.S. Cl.
CPC ............ *B60W 40/08* (2013.01); *B60W 40/06* (2013.01); *B60W 50/0097* (2013.01); *B60W 2040/0872* (2013.01)

(58) Field of Classification Search
CPC .................................... B60G 1/00; A61B 1/00
See application file for complete search history.

(56) References Cited

U.S. PATENT DOCUMENTS

| | | | |
|---|---|---|---|
| 7,872,764 B2 | 1/2011 | Higgins-Luthman et al. | |
| 9,533,539 B2 | 1/2017 | Eng et al. | |
| 2011/0213511 A1 | 9/2011 | Visconti et al. | |
| 2011/0224875 A1 | 9/2011 | Cuddihy et al. | |
| 2013/0103259 A1* | 4/2013 | Eng .................... | B60G 17/0165 701/37 |
| 2014/0195112 A1 | 7/2014 | Lu et al. | |
| 2014/0288450 A1* | 9/2014 | Freeman ............ | A61B 5/04012 600/509 |
| 2014/0297116 A1 | 10/2014 | Anderson et al. | |
| 2015/0195456 A1* | 7/2015 | Koskinen ........... | H04N 5/23267 348/208.5 |
| 2017/0151850 A1 | 6/2017 | Deigmoller et al. | |
| 2018/0079272 A1* | 3/2018 | Aikin ................. | B60G 17/0195 |
| 2018/0348759 A1* | 12/2018 | Freeman ............ | G01C 21/3415 |
| 2019/0047498 A1* | 2/2019 | Alcaidinho ............... | G06F 3/14 |

* cited by examiner

*Primary Examiner* — Shirley Lu

(74) *Attorney, Agent, or Firm* — Brooks Kushman P.C.

(57) ABSTRACT

A method and system include a biometric monitor monitoring an occupant of the vehicle and a vision detector detecting a condition of an upcoming road segment. A controller determines an adjustment to the biometric monitor for the biometric monitor to counteract an expected effect that the condition of the upcoming road segment will have on the biometric monitor in monitoring the occupant when the vehicle drives over the upcoming road segment. The controller adjusts the biometric monitor according to the adjustment such that the biometric monitor is adjusted in monitoring the occupant according to the adjustment as the vehicle drives over the upcoming road segment. The controller may determine an adaptation to a suspension assembly of the vehicle for the suspension assembly to counteract the expected effect and adapt the suspension assembly according to the adaptation. The adjustment to the biometric monitor is modified accordingly.

20 Claims, 4 Drawing Sheets

METHOD AND SYSTEM FOR PROACTIVELY ADJUSTING VEHICLE OCCUPANT BIOMETRIC MONITOR IN VIEW OF UPCOMING ROAD CONDITIONS

TECHNICAL FIELD

The present invention relates to a vehicle having a biometric monitor for monitoring an occupant of the vehicle.

BACKGROUND

A vehicle may have a biometric monitor for monitoring physical characteristics, such as heart rate and respiratory rate, of an occupant of the vehicle. The biometric monitor may not properly monitor the physical characteristics when the vehicle jostles such as when the vehicle is driving over a bumpy road. The jostling movement of the vehicle introduces noise to the biometric monitor causing it to either erroneously or be unable to monitor the physical characteristics.

The vehicle includes a suspension assembly to reduce jostling movement of the vehicle. To make the ride even smoother, the suspension assembly may be a suspension assembly that can be adapted as the vehicle encounters different road conditions. A suspension assembly which is adapted based on road conditions as they are encountered employs a "feed-back" control system. An issue is that it can be difficult to make the appropriate adaptions to the suspension assembly in a short amount of time. This is because the lag time between when a road condition is encountered and when the feed-back control system makes the adaption may be too long.

SUMMARY

A method for a vehicle includes monitoring, with a biometric monitor in the vehicle, an occupant of the vehicle. The method includes detecting a condition of an upcoming road segment; determining an adjustment to the biometric monitor for the biometric monitor to counteract an expected effect that the condition of the upcoming road segment will have on the biometric monitor in monitoring the occupant of the vehicle when the vehicle drives over the upcoming road segment; and adjusting the biometric monitor according to the adjustment such that the biometric monitor is adjusted in monitoring the occupant of the vehicle according to the adjustment as the vehicle drives over the upcoming road segment.

The method may further include monitoring an effectiveness of the adjustment of the biometric monitor in counteracting the expected effect. Upon a condition of a subsequent upcoming road segment similar to the detected condition being detected, the method includes modifying the adjustment based on the monitored effectiveness and adjusting the biometric monitor according to the modified adjustment such that the biometric monitor is adjusted in monitoring the occupant of the vehicle according to the modified adjustment as the vehicle drives over the subsequent upcoming road segment.

Determining the adjustment to the biometric monitor may involve using artificial intelligence. This artificial intelligence may be deployed initially at the individual vehicle level using unsupervised techniques for fast adaptations with later updates coming from remote computation that can employ both supervised and/or unsupervised methods to enhance the future accuracy of the system. Methods can include clustering and dimension reduction for unsupervised applications and classification and regression for supervised approaches.

The method may further include determining an adaptation to a suspension assembly of the vehicle for the suspension assembly to counteract the expected effect; adapting the suspension assembly according to the adaptation such that the suspension assembly is adapted according to the adaptation as the vehicle drives over the upcoming road segment. In this case, determining the adjustment to the biometric monitor includes modifying the adjustment according to an expected counteraction that the adapted suspension assembly will have on the expected effect.

The method may further include monitoring an effectiveness of the adaptation of the suspension assembly in counteracting the expected effect. Upon a condition of a subsequent upcoming road segment similar to the detected condition being detected, the method includes modifying the adaptation based on the monitored effectiveness and adapting the suspension assembly according to the modified adaptation such that the suspension assembly is adapted according to the modified adaptation as the vehicle drives over the subsequent upcoming road segment.

Determining the adaptation to the suspension assembly may involve using artificial intelligence.

The condition of the upcoming road segment may include at least one of an object in the upcoming road segment, a surface change of the upcoming road segment, and a feature change of the upcoming road segment.

Detecting the condition of the upcoming road segment may include viewing the upcoming road segment with a camera of the vehicle.

Another method for a vehicle includes monitoring, with a biometric monitor in the vehicle, an occupant of the vehicle; detecting a condition of an upcoming road segment; determining an adaptation to a suspension assembly of the vehicle for the suspension assembly to counteract an expected effect that the condition of the upcoming road segment will have on the biometric monitor in monitoring the occupant of the vehicle when the vehicle drives over the upcoming road segment; determining an adjustment to the biometric monitor for the biometric monitor to counteract the expected effect; modifying the adjustment according to an expected counteraction that the adapted suspension assembly will have on the expected effect; adapting the suspension assembly according to the adaptation such that the suspension assembly is adapted according to the adaptation as the vehicle drives over the upcoming road segment; and adjusting the biometric monitor according to the adjustment as modified such that the biometric monitor is adjusted in monitoring the occupant of the vehicle according to the adjustment as modified as the vehicle drives over the upcoming road segment.

Determining and modifying the adjustment to the biometric monitor may involve using artificial intelligence. Determining the adaptation to the suspension assembly may involve using artificial intelligence.

A system for a vehicle having a vision detector configured to detect a condition of an upcoming road segment is provided. The system includes a biometric monitor configured to monitor an occupant of the vehicle. The system further includes a controller in communication with the biometric monitor and the vision detector. The controller configured to determine an adjustment to the biometric monitor for the biometric monitor to counteract an expected effect that the condition of the upcoming road segment will have on the biometric monitor in monitoring the occupant of the vehicle when the vehicle drives over the upcoming road segment and to adjust the biometric monitor according to the adjustment such that the biometric monitor is adjusted in monitoring the occupant of the vehicle according to the adjustment as the vehicle drives over the upcoming road segment.

The controller may be further configured to monitor an effectiveness of the adjustment of the biometric monitor in counteracting the expected effect. Upon a condition of a subsequent upcoming road segment similar to the detected condition being detected by the vision detector, the controller is further configured to modify the adjustment based on the monitored effectiveness and adjust the biometric monitor according to the modified adjustment such that the biometric monitor is adjusted in monitoring the occupant of the vehicle according to the modified adjustment as the vehicle drives over the subsequent upcoming road segment.

The controller may be further configured to determine the adjustment to the biometric monitor using artificial intelligence.

The controller may be further configured to determine an adaptation to a suspension assembly of the vehicle for the suspension assembly to counteract the expected effect and to adapt the suspension assembly according to the adaptation such that the suspension assembly is adapted according to the adaptation as the vehicle drives over the upcoming road segment. In this case, in determining the adjustment to the biometric monitor the controller is further configured to modify the adjustment according to an expected counteraction that the adapted suspension assembly will have on the expected effect.

The controller may be further configured to monitor an effectiveness of the adaptation of the suspension assembly in counteracting the expected effect. Upon a condition of a subsequent upcoming road segment similar to the detected condition being detected by the vision detector, the controller is further configured to modify the adaptation based on the monitored effectiveness and adapt the suspension assembly according to the modified adaptation such that the suspension assembly is adapted according to the modified adaptation as the vehicle drives over the subsequent upcoming road segment.

The controller may be further configured to determine the adaptation to the suspension assembly using artificial intelligence.

The occupant of the vehicle may be seated in a vehicle seat of the vehicle with the biometric monitor directed towards the vehicle seat.

DETAILED DESCRIPTION

Detailed embodiments of the present invention are disclosed herein; however, it is to be understood that the disclosed embodiments are merely exemplary of the present invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

In accordance with embodiments, a vehicle includes a biometric monitor for monitoring an occupant of the vehicle and a method and system detect an upcoming road segment and use that information to control aspects of the biometric monitor in monitoring the occupant of the vehicle. An example is a vision detector of the vehicle having cameras and/or sensors detects a condition (potholes, sharp turns, steep inclines, etc.) of the upcoming road segment. A vehicle controller proactively (i.e., feed-forward or preview-type) controls the biometric monitor based on the detected condition of the upcoming road segment. Because the method and system assess the upcoming road segment that is ahead of the vehicle, as opposed to the road segment currently being encountered by the vehicle, the method and system may improve performance of the biometric monitor in monitoring the occupant of the vehicle by anticipating and preparing the biometric monitor for road conditions before they are actually encountered. The biometric monitor is thereby adjusted when the vehicle drives over the upcoming road segment to counteract an expected effect that the condition of the upcoming road segment will have on the biometric monitor in monitoring the occupant of the vehicle as the vehicle drives over the upcoming road segment.

Figure 1:
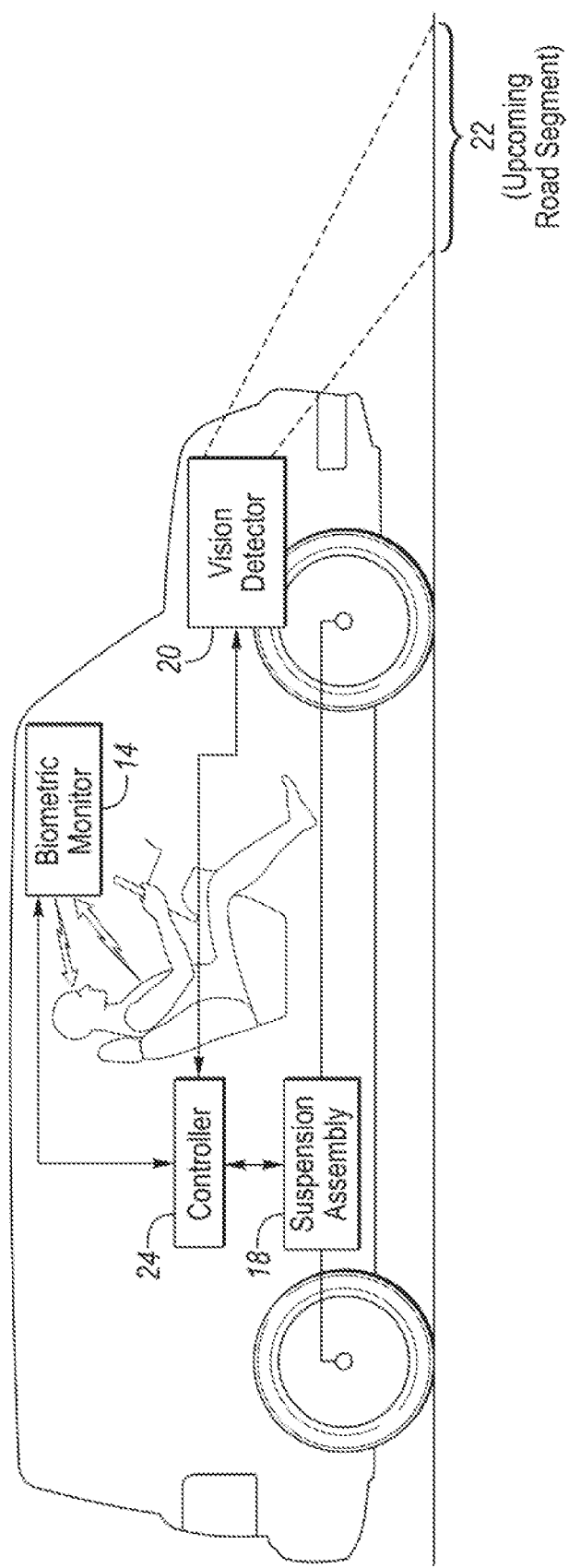
FIG. 1 illustrates a block diagram of a vehicle having a system including a biometric monitor for monitoring an occupant of the vehicle, a suspension assembly for smoothing the ride of the vehicle, a vision detector for detecting a condition of an upcoming road segment, and a controller for proactively controlling the biometric monitor and the suspension assembly based on the condition of the upcoming road segment.

Referring now to FIG. 1, a block diagram of a vehicle 10 having a system 12 in accordance with an embodiment is shown. System 12 includes a biometric monitor 14 for monitoring an occupant 16 of vehicle 10, a suspension assembly 18 for smoothing the ride of the vehicle, and a vision detector 20 for detecting a condition of an upcoming road segment 22. System 12 further includes a controller 24 for proactively controlling biometric monitor 14 and suspension assembly 18 based on the condition of upcoming road segment 22.

Biometric monitor 14 includes sensors configured to wirelessly monitor physical characteristics of occupant 16 of vehicle 10. For instance, occupant 16 sits in a vehicle seat of vehicle 10 and the sensors of biometric monitor 14 are located on the vehicle dashboard facing the occupant. The sensors of biometric monitor 14 may be radar sensors employing radio-frequency (RF) sensing to sense the physical characteristics of occupant 16. The sensed physical characteristics may include the heart rate and respiratory rate of occupant 16. Other sensed physical characteristics may include stress and drowsiness of occupant 16.

The physical characteristics of occupant 16 sensed by biometric monitor 14 may be used by a seat controller to adjust the vehicle seat, such as by positioning and heating and massage functions, to improve the comfort of the occupant sitting in the vehicle seat. The sensed physical characteristics may be indicative of a health or other emergency situation involving occupant 16. In this case, a telematics control system of vehicle 10 may be made aware of the health or other emergency situation from the sensed physical characteristics and may take appropriate actions such as warning occupant 16 and/or wirelessly contacting a health care professional or family member.

Suspension assembly 18 couples the wheels of vehicle 10 to the vehicle body. Suspension assembly 18 may include one of any number of different suspension-related components or parts. For example, suspension assembly 18 may include dampers, shock-absorbers, and/or other actuators in an active or semi-active vehicle suspension system that helps control the vertical movement of the wheels in response to the road surface. Suspension assembly 18 may be an adaptive (i.e., active) suspension assembly which can be controlled on-the-fly as vehicle 10 is driven over a road. For example, suspension assembly 18 as an adaptive suspension assembly can be controlled by altering the amount of electrical current and/or voltage provided to the suspension assembly; increasing the current raises compression/rebound rates of the suspension assembly, while decreasing the current softens the effect of the suspension assembly.

Vision detector 20 may detect, inspect, assess, and/or otherwise evaluate an upcoming road segment 22 and provide controller 24 with road information that pertains to upcoming road segment. For example, vision detector 20 may include a stereo vision system having two or more cameras (e.g., several megapixel black and white CMOS cameras) and captures digital images of upcoming road segment 22 located in front of vehicle 10. For instance, upcoming road segment 22 may be located approximately one to twenty meters in front of vehicle 10. The use of multiple cameras provides several different perspectives of the same image which can then be stitched, blended, and/or otherwise combined in much the same manner as that used by human eyes. The cameras may be mounted in various locations around vehicle 10, including at a rear-view mirror assembly located near a top-center portion of the front windshield of the vehicle, the front bumper of the vehicle, and the like.

Integrated vision systems are available that include multiple cameras and a module for processing the camera output, where the cameras and the module are all integrated into a single package or unit. Vision detector 20 may be part of an Advanced Driver Assisted System (ADAS) of vehicle 10 or may be part of some other component, device, module, and/or system in the vehicle, like a vehicle safety system or collision avoidance system. Additionally, or alternatively to being a camera-based system, vision detector 20 can include a light detection and ranging (LIDAR) device, radio detection and ranging (RADAR) device, some other evaluation device, or a combination thereof.

Controller 24 is in communication with biometric monitor 14, suspension assembly 18, and vision detector 20. Controller 24 may be a vehicle controller that may include any variety of electronic processing devices, memory devices, input/output (I/O) devices, and/or other known components, and may perform various control and/or communication related functions. In an exemplary embodiment, controller 24 includes an electronic memory device that stores sensor readings from biometric monitor 14, readings indicative of vehicle jostling which may be derived from suspension assembly 18 or from other detectors, images from vision detector 20, look-up tables or other data structures, processes such as the processes described below with reference to FIG. 3, and/or the like.

The memory device of controller 24 may store pertinent characteristics and background information pertaining to biometric monitor 14 such as occupant monitoring related parameters and pertinent characteristics and background information pertaining to vehicle 10 such as suspension-related parameters and settings.

Controller 24 may also include an electronic processing device (e.g., a microprocessor, a microcontroller, an application specific integrated circuit (ASIC), etc.) that executes instructions for software, firmware, programs, algorithms, scripts, etc. that are stored in the memory device and may govern the methods described herein. Controller 24 may be electronically connected to other vehicle devices, modules, and systems via suitable vehicle communications and can interact with them when required. Controller 24 may be a stand-alone vehicle electronic module, it may be incorporated or included within another vehicle electronic module, or it may be part of a larger network or system such as a vehicle safety system or a driver assistance system.

Figure 2:
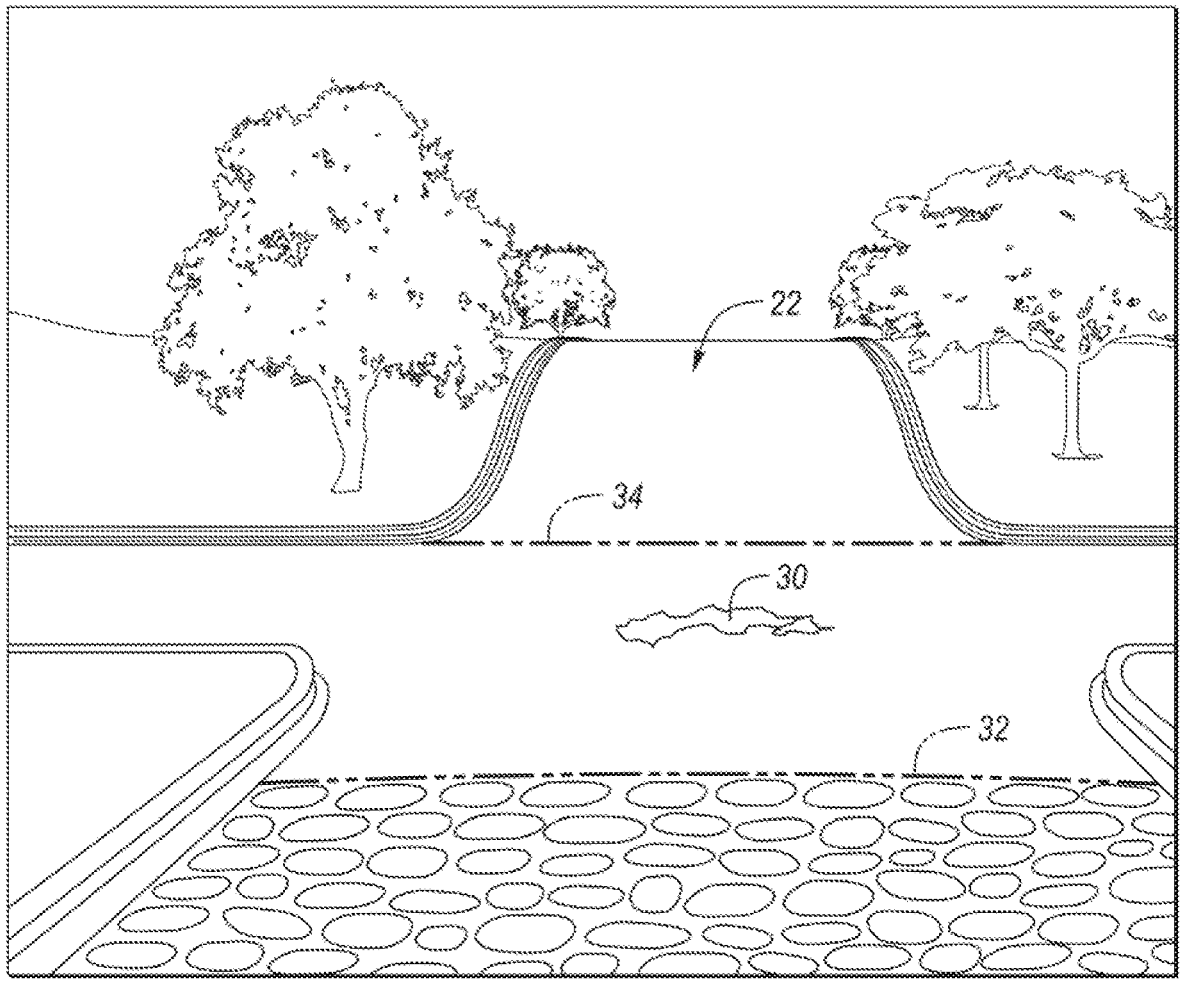
FIG. 2 illustrates a view of an exemplary upcoming road segment that includes an object in the road, a road surface change, and a road feature change.

Referring now to FIG. 2, with continual reference to FIG. 1, an exemplary embodiment of upcoming road segment 22 is shown. Upcoming road segment 22 includes an object 30 in the road, a road surface change 32, and a road feature change 34. Upcoming road segment 22 is in front of vehicle 10 and the vehicle will be driving over the upcoming road segment in the near future.

Vision detector 20 inspects upcoming road segment 22 to detect the condition of the upcoming road segment. Vision detector 20 generates road information pertaining to upcoming road segment 22. The road information includes all types of images, coordinates, data, and/or other information that pertains to upcoming road segment 22. Some examples of road information include raw camera images (stitched or non-stitched), processed camera images, and/or specific pieces of information that have been extracted or deduced from the camera images.

The road information may reveal or identify different types of road conditions in upcoming road segment 22 such as objects in the road, road surface changes, and/or road feature changes. Beginning with the category of objects in the road, the road information pertains to objects such as potholes, cracks, bumps, manhole covers, drains, debris, etc., located in upcoming road segment 22. In the example illustrated in FIG. 2, object 30 is a pothole located in upcoming road segment 22. Vision detector 20 may provide controller 24 with road information indicative of a position of object 30 (e.g., the x, y, z coordinates for each of the image pixels which correspond to the object), a size of the object, a distance to the object (e.g., a distance or time to impact for vehicle 10 and the object), and/or a projected wheel path as it relates to the object (e.g., whether the driver-side wheels, passenger-side wheels, or both will encounter the object according to a path-prediction feature).

Regarding the category of road surface changes, the road information pertains to various road surface changes, like transitions between concrete, asphalt, cobblestone, gravel, dirt, etc. In the example illustrated in FIG. 2, road surface change 32 involves the road surface changing to cobblestone. Vision detector 20 may provide controller 24 with road information indicative of a change or transition in the surface of upcoming road segment 22, such as a change from one material to another that can cause chatter or other undesirable effects. Some examples of road information that may indicate a change in the road surface include a description of the road surface change (e.g., a qualitative or quantitative description of road surface change 32), a position of the road surface change (e.g., x, y, z coordinates for each of the pixels along the road surface change), a distance to the road surface change (e.g., a distance or time to impact for vehicle 10 and the road surface change), and/or the projected wheel path as it relates to the road surface change (e.g., whether the driver-side wheels, passenger-side wheels, or both will encounter the road surface change according to a path-prediction feature).

One way to provide a qualitative description of road surface change 32 is to consider the attributes of the different sections of upcoming road surface 22 (e.g., the z-axis coordinates), and then categorize the different sections based on that information; such an approach could result in classifications like "concrete," "cobblestone" and "gravel," and could reveal transitions or changes between different surfaces. One way to provide a quantitative description involves mathematically evaluating the heights of different upcoming road surface sections and providing some numerical description of those heights (e.g., calculating an average height or a variance in height for a particular section). Road surface changes may also pertain to weather-related conditions, such as if the road is wet, snowy, icy, etc., and may be discernable from the road information.

Regarding the category of road feature changes, the road information pertains to changes or transitions in road features, like sharp turns or bends in the road. In the example illustrated in FIG. 2, road feature change 34 involves a steep incline or hill. Vision detector 20 may provide controller 24 with road information indicative of a description of road feature change 34 (e.g., a qualitative or quantitative description of the incline or hill), a position of the road feature change (e.g., x, y, z coordinates for each of the pixels at the incline or hill), a distance to the road feature change (e.g., a distance or time to impact for vehicle 10 and the incline or hill), and/or the projected wheel path as it relates to the road feature change (e.g., whether the driver-side wheels, passenger-side wheels, or both will encounter the incline or hill using a path-prediction feature). The road feature change can be simply identified according to its type or category (e.g., curve, bend, incline, decline, etc.) or it could be more descriptive and describe it in terms of a large, medium or small curve, bend, incline, decline, etc.; these are both qualitative descriptions. It is also possible for the road information to quantitatively describe road feature change 34 such as in terms of numerical data regarding the grade, angle, or elevation change of the incline or hill, or the radius or angle of an upcoming bend in the road; these are examples of quantitative descriptions.

The communication and interaction between vision detector 20 and controller 24 may be arranged according to any number of different ways. The road information from vision detector 20 may be augmented or supplemented with road information from other sources, like a navigation system of vehicle 10. By using output from vision detector 20 in conjunction with that from a navigation system, a fuller or more complete picture of upcoming road segment 22 may be developed. This can be particularly helpful if vision detector 20 is temporarily obstructed or experiences a malfunction so that it is unable to produce usable images.

Referring now back to FIG. 1, a general overview of the operation of system 12 will now be provided. System 12 represents an innovative concept to proactively control the settings and parameters (e.g., variable gain, filter, etc.) of biometric monitor 14 (e.g., radar) based biometrics and suspension assembly 18 based on the forward-facing road conditions detected by vision detector 20 (e.g., the ADAS such as cameras, radar, and lidar based sensors (outside vehicle 10)). System 12 is operational in all road conditions (stable, rough, city, rural, subdivision, etc.) and in all weather and light conditions.

In operation, vision detector 20 (i.e., the ADAS based sensors) detects the conditions of upcoming road segment 22. In this regard, vision detector 20 assesses the incoming road and traffic conditions in front of vehicle 10 during both the day and at night, considering the changing light conditions.

Controller 24 analyzes the road conditions visualized by vision detector 20. Controller 24 determines, based on the road and traffic conditions, the likelihood of vehicle 10 being jostled and the anticipated characteristics of the vehicle jostling motion. Controller 24 then determines optimization adjustments of the settings and parameters for biometric monitor 14 and/or suspension assembly 18 for the biometric monitor and/or the suspension assembly to be adjusted to counteract the effects that the anticipated characteristics of the jostling motion will have on the biometric monitor in monitoring occupant 16 of vehicle 10. Controller 24 then applies preemptive optimization adjustments to biometric monitor 14 and/or suspension assembly 18 in preparation for approaching road and traffic conditions. In this way, biometric monitor 14 and/or suspension assembly 18 are adjusted proactively as opposed to reactively.

As such, suspension assembly 18, as an adaptive suspension assembly, is optimized based on approaching road conditions visualized by vision detector 20 (e.g., on-board forward facing ADAS). Vision detector 20, such as in the form of an integrated ADAS, allows for proactive signal processing by optimizing the settings of biometric monitor 14. Proactive optimization of the settings of biometric monitor 14 prevents corruption of heart rate and respiration measurement data due to saturation otherwise caused by the jostling motion of vehicle 10. Selection and adjustment of filtering schemes and parameters for biometric monitor 14 is based on anticipated jostling motion profile of vehicle 10. In sum, properly optimized settings for biometric monitor 14 ensures that heart rate and respiration data obtained by the biometric monitor (e.g., radar) is usable for monitoring occupant 16.

In embodiments, controller 24 is, or at least part of, an artificial intelligence (AI) computerized system. Controller 24 uses AI in analyzing the images and sensor data of upcoming road segment 22 to determine how the approaching road and traffic conditions will affect the motion of biometric monitor 14 for heart rate and respiration detection and/or vehicle 10 in general. Controller 24 uses AI to learn from each new road and traffic condition the most optimal signal-to-noise (SNR) ratio for settings adjustment of biometric monitor 14. Controller 24 uses AI to continually re-evaluate "optimal" settings for biometric monitor 14. Similarly, controller 24 uses AI to learn from each new road and traffic condition the most optimal adaptation of suspension assembly 18 for those conditions. Controller 24 uses AI to continually re-evaluate "optimal" settings for suspension assembly 18. Further, using AI, controller 24 learns how to perform complex dual adaptive schemes for biometric monitor 14 and suspension assembly 18 simultaneously.

Figure 3:
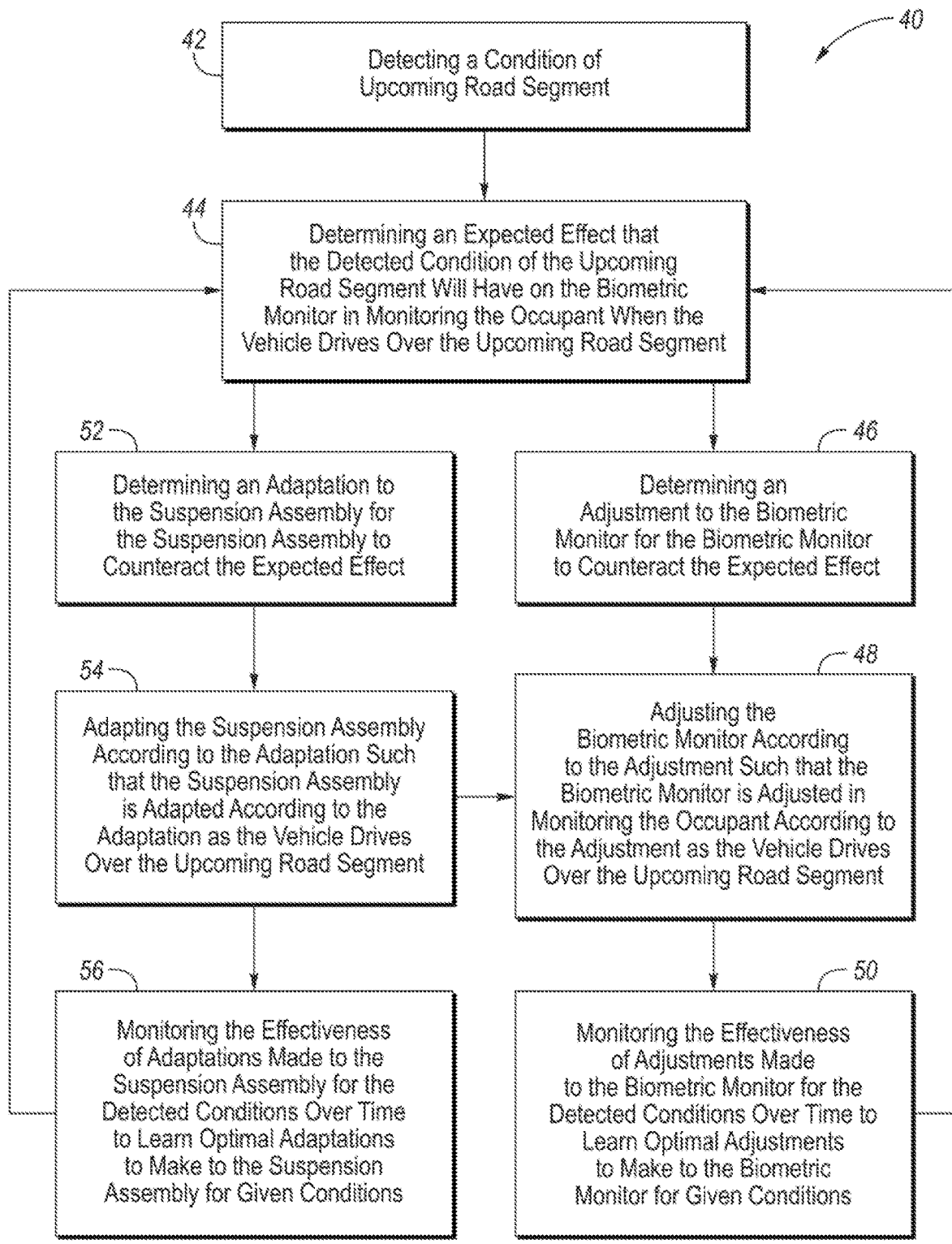
FIG. 3 illustrates a flowchart depicting representative operations of the method and system for proactively adjusting the biometric monitor and the suspension assembly based on the condition of the upcoming road segment.

Referring now to FIG. 3, with continual reference to FIGS. 1 and 2, a flowchart 40 depicting representative operations of a method and system for proactively adjusting biometric monitor 14 and suspension assembly 18 based on the condition of an upcoming road segment 22 in accordance with embodiments is shown. The operations include vision detector 20 (e.g., on-board ADAS vehicle sensors) detecting a condition of upcoming road segment 22, as indicated in block 42. For instance, with reference to FIG. 2, a condition of upcoming road segment may include an object in the road, a road surface change, and/or a road feature change.

The operations further include controller 24 determining an expected effect that the detected condition of upcoming road segment 22 will have on biometric monitor 14 in monitoring occupant 16 when vehicle 10 drives over the upcoming road segment, as indicated in block 44. Controller 24 then determines an adjustment to biometric monitor 14 for the biometric monitor to counteract the expected effect that the detected condition of upcoming road segment 22 will have on the biometric monitor in monitoring occupant 16, as indicated in block 46. Controller 24 then adjusts biometric monitor 14 according to the adjustment such that the biometric monitor is adjusted in monitoring occupant 16 according to the adjustment as vehicle 10 drives over upcoming road segment 22, as indicated in block 48.

Controller 24 may use AI to learn, over time, and with every new road and traffic condition, how best to optimize the adjustments of biometric monitor 14. In this case, controller 24 monitors the effectiveness of adjustments made to biometric monitor 14 for the detected conditions over time to learn optimal adjustments to make to the biometric monitor for given conditions, as indicated by block 50. For example, controller 24 monitors the effectiveness in maintaining the SNR of biometric monitor 14 from an adjustment made to the biometric monitor for a detected condition. If the SNR is maintained poorly, then controller 24 learns to change the adjustment for the same type of detected condition. This process is performed over time for controller 24 to learn the optimal adjustment which will maintain the SNR for an encountered condition that is the same or similar to the originally detected condition.

In this way, controller 24 learns from each road and traffic condition and subsequent optimization adjustment, allowing for continued refinement of the adjustments made to biometric monitor 14. Continually refining the adjustment (e.g., the correct gain value) to biometric monitor 14 allows for the most optimal result (e.g., highest gain (and therefore strongest signal) without saturation of the data). This insures the best data provided by biometric monitor 14 for further analysis of heart rate and respiratory rate of occupant 16.

Suspension assembly 18 may be an adaptive suspension assembly (i.e., a suspension assembly that is capable of being controlled on-the-fly as vehicle 10 is driven over the road). In this case, the operations may further include controller 24 determining an adaptation to suspension assembly 18 for the suspension assembly to counteract the expected effect that the detected condition of upcoming road segment 22 will have on biometric monitor 14 in monitoring occupant 16, as indicated in block 52. Controller 24 then adapts suspension assembly 18 according to the adaptation such that the suspension assembly is adapted according to the adaptation as vehicle 10 drives over upcoming road segment 22, as indicated in block 54.

In view of the operations of blocks 52 and 54, the adjustment to be made to biometric monitor 14, determined in block 46, is modified according to an expected counteraction that the adapted suspension assembly 18 will have on the expected effect that the condition of upcoming road segment 22 will have on the biometric monitor. In turn, biometric monitor 14 is adjusted in block 48 according to the modified adjustment. Thus, suspension assembly 18 is adapted to limit jostling movement of vehicle 10 and biometric monitor 14 is adjusted based on how the suspension assembly is adapted and how likely the adapted suspension assembly is likely to limit the jostling movement of the vehicle. Controller 24 may use AI to learn, over time, and with every new road and traffic condition, how to best optimize the adjustments of biometric monitor 14 based on the adaptations to suspension assembly 18 over time to provide the strongest signal for the best results.

As an example, with reference to FIG. 2 which illustrates an upcoming road segment 22 having object 30 in the form of a pothole, the following description describes how system 12 works to ensure that the settings of biometric monitor 14 will not saturate and corrupt the measurement signal indicative of the physical characteristics of occupant 16 when controller 24 has learning capabilities for the biometric monitor. The sensors of vision detector 20 which are focused on the outside of vehicle 10 detect the approaching pothole. Controller 24 takes in this information and proactively prepares suspension assembly 18 to handle the approaching road conditions by adapting, for example, the suspension shock and spring settings to a predetermined value for "pothole". Based on this adjustment, controller 24 adjusts the settings of biometric monitor 14 to prevent the measurement signal from saturating.

As controller 24 has AI learning capabilities for the settings of biometric monitor 14, the controller monitors how different road conditions cause suspension assembly 18 to be adapted and whether the subsequent adjustment of the biometric monitor was most optimal or could be improved. The next time vehicle 10 approaches a pothole, the same adaptation will be made to suspension assembly 18, however, the adjustment to biometric monitor 14 will differ in favor of a more optimal adjustment.

Controller 24 may also use AI to learn, over time, and with every new road and traffic condition, how best to optimize the adaptations of suspension assembly 18. In this case, controller 24 monitors the effectiveness of adaptations made to suspension assembly 18 for the detected conditions over time to learn optimal adaptations to make to the suspension assembly for given conditions, as indicated by block 56. For example, controller 24 monitors the effectiveness in maintaining the SNR of biometric monitor 14 from an adaptation made to the suspension assembly for a detected condition. If the SNR is maintained poorly, then controller 24 learns to change the adaptation for the same type of detected condition. This process is performed over time for controller 24 to learn the optimal adaptation which will maintain the SNR for an encountered condition that is the same or similar to the originally detected condition.

In this way, controller 24 learns from each road and traffic condition and subsequent optimization adaptation, allowing for continued refinement of the adaptations made to suspension assembly 18. Continually refining the adaptation (e.g., the correct shock and spring settings) to suspension assembly 18 creates the smoothest ride of vehicle 10 and therefore limits noise and the potential for saturation in the measured data signal of biometric monitor 14.

System 12 may thus include an AI-learning biometric monitor 14 and an AI-learning adaptable suspension assembly 18. In this case, suspension assembly 18 improves its ability to mitigate potential jostling movements of vehicle 10 due to road and traffic conditions over time as it learns about those different conditions. Biometric monitor 14 also learns how best to adjust its gain to ensure the most optimized signal based on how suspension assembly 18 learns to limit the jostling movement of vehicle 10. Suspension assembly 18 learns from the road conditions and biometric monitor 14 learns from the suspension assembly. This provides a layered approach to optimization adjustments.

As another example, with reference to FIG. 2 which illustrates an upcoming road segment 22 having object 30 in the form of a pothole, the following description describes how system 12 works to ensure that the settings of biometric monitor 14 will not saturate and corrupt the measurement signal indicative of the physical characteristics of occupant 16 when controller 24 has learning capabilities for both of the biometric monitor and suspension assembly 18. Vision detector 20 detects the approaching pothole. Controller 24 takes in this information and proactively prepares suspension assembly 18 to handle the approaching road conditions by adapting the suspension shock and spring settings.

Because controller 24 has learning capabilities for suspension assembly 18, the controller monitors the motion of vehicle 10 (via sensors, for example) after the suspension adaptations have been made for different road conditions and continually improves the adaptations so the most optimal motion pattern can be obtained for any specific or set of road/traffic conditions. Based on the suspension adaptation, controller 24 adapts the settings of biometric monitor 14 to prevent the measurement signal from saturating.

As controller 24 has AI learning capabilities for the settings of both biometric sensor 14 and suspension assembly 18, the controller monitors how different road conditions cause the suspension assembly to be adapted and whether the subsequent adjustment of biometric monitor 14 was most optimal or could be improved. The next time vehicle 10 approaches a pothole, the adaptation to suspension assembly 18 will differ in favor of a more optimal motion pattern and the adjustment to biometric monitor 14 will differ in favor of a more optimal gain setting based on the suspension setting.

Figure 4:
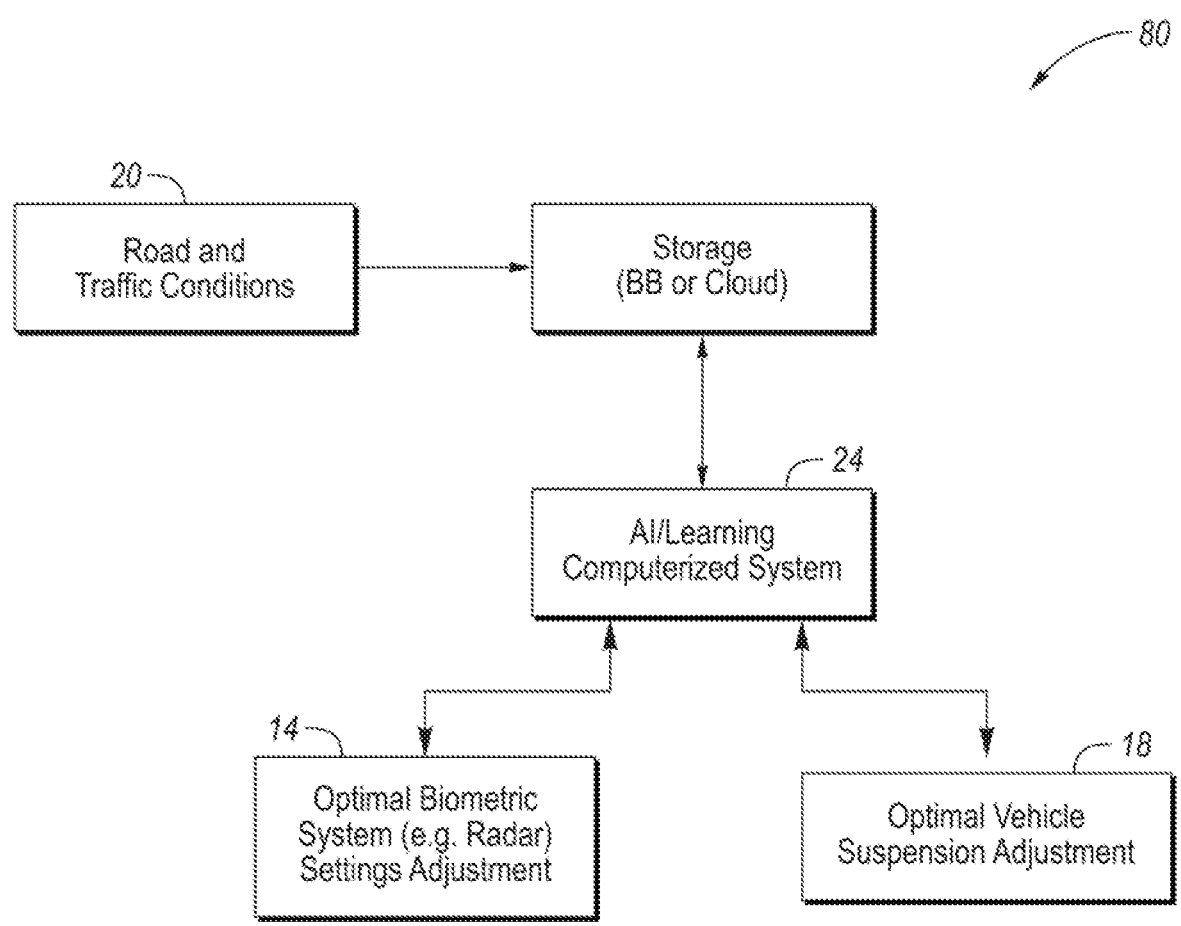
FIG. 4 illustrates a flowchart of processing steps which may be carried out by the controller to proactively control the biometric monitor and the suspension assembly based on the condition of the upcoming road segment.

Referring now to FIG. 4, with continual reference to FIG. 1, a flowchart 80 of processing steps which may be carried out for controller 24 to proactively control biometric monitor 14 and suspension assembly 18 based on the condition of upcoming road segment 22 is shown.

While exemplary embodiments are described above, it is not intended that these embodiments describe all possible forms of the present invention. Rather, the words used in the specification are words of description rather than limitation, and it is understood that various changes may be made without departing from the spirit and scope of the present invention. Additionally, the features of various implementing embodiments may be combined to form further embodiments of the present invention.

What is claimed is:

1. A method for a vehicle, the method comprising:
monitoring, with a biometric monitor in the vehicle, an occupant of the vehicle;
detecting, by a vision detector of the vehicle, a condition of an upcoming road segment that the vehicle will be driving over;
determining, by a controller of the vehicle, based on the condition of the upcoming road segment, an anticipated jostling motion that the vehicle will have when the vehicle drives over the upcoming road segment;
determining, by the controller, an adjustment to the biometric monitor for the biometric monitor to counteract an expected effect that the anticipated jostling motion of the vehicle will have on the biometric monitor in monitoring the occupant of the vehicle when the vehicle drives over the upcoming road segment; and
adjusting, by the controller, the biometric monitor according to the adjustment such that the biometric monitor is adjusted in monitoring the occupant of the vehicle according to the adjustment as the vehicle drives over the upcoming road segment.

2. The method of claim 1 further comprising:
monitoring, by the controller, an effectiveness of the adjustment of the biometric monitor in counteracting the expected effect; and
upon detecting a condition of a subsequent upcoming road segment similar to the detected condition, modifying, by the controller, the adjustment based on the monitored effectiveness and adjusting, by the controller, the biometric monitor according to the modified adjustment such that the biometric monitor is adjusted in monitoring the occupant of the vehicle according to the modified adjustment as the vehicle drives over the subsequent upcoming road segment.

3. The method of claim 1 wherein:
determining the adjustment to the biometric monitor involves using artificial intelligence.

4. The method of claim 1 further comprising:
determining, by the controller, an adaptation to a suspension assembly of the vehicle for the suspension assembly to counteract the expected effect;
adapting, by the controller, the suspension assembly according to the adaptation such that the suspension assembly is adapted according to the adaptation as the vehicle drives over the upcoming road segment; and
wherein determining the adjustment to the biometric monitor includes modifying the adjustment according to an expected counteraction that the adapted suspension assembly will have on the expected effect.

5. The method of claim 4 further comprising:
monitoring, by the controller, an effectiveness of the adaptation of the suspension assembly in counteracting the expected effect; and
upon detecting a condition of a subsequent upcoming road segment similar to the detected condition, modifying, by the controller, the adaptation based on the monitored effectiveness and adapting the suspension assembly according to the modified adaptation such that the suspension assembly is adapted according to the modified adaptation as the vehicle drives over the subsequent upcoming road segment.

6. The method of claim 4 wherein:
determining the adjustment to the biometric monitor involves using artificial intelligence.

7. The method of claim 6 wherein:
determining the adaptation to the suspension assembly involves using artificial intelligence.

8. The method of claim 1 wherein:
the condition of the upcoming road segment includes at least one of an object in the upcoming road segment, a surface change of the upcoming road segment, and a feature change of the upcoming road segment.

9. The method of claim 1 wherein:
the vision detector of the vehicle includes a camera of the vehicle.

10. A system for a vehicle having a vision detector configured to detect a condition of an upcoming road segment that the vehicle will be driving over, the system comprising:
a biometric monitor configured to monitor an occupant of the vehicle; and
a controller in communication with the biometric monitor and the vision detector, the controller configured to determine, based on the condition of the upcoming road segment, an anticipated jostling motion that the vehicle will have when the vehicle drives over the upcoming road segment, to determine an adjustment to the biometric monitor for the biometric monitor to counteract an expected effect that the anticipated jostling motion of the vehicle will have on the biometric monitor in monitoring the occupant of the vehicle when the vehicle drives over the upcoming road segment, and to adjust the biometric monitor according to the adjustment such that the biometric monitor is adjusted in monitoring the occupant of the vehicle according to the adjustment as the vehicle drives over the upcoming road segment.

11. The system of claim 10 wherein:
the controller is further configured to monitor an effectiveness of the adjustment of the biometric monitor in counteracting the expected effect; and
upon a condition of a subsequent upcoming road segment similar to the detected condition being detected by the vision detector, the controller is further configured to modify the adjustment based on the monitored effectiveness and adjust the biometric monitor according to the modified adjustment such that the biometric monitor is adjusted in monitoring the occupant of the vehicle according to the modified adjustment as the vehicle drives over the subsequent upcoming road segment.

12. The system of claim 10 wherein:
the controller is further configured to determine the adjustment to the biometric monitor using artificial intelligence.

13. The system of claim 10 wherein:
the controller is further configured to determine an adaptation to a suspension assembly of the vehicle for the suspension assembly to counteract the expected effect and to adapt the suspension assembly according to the adaptation such that the suspension assembly is adapted according to the adaptation as the vehicle drives over the upcoming road segment; and
wherein in determining the adjustment to the biometric monitor the controller is further configured to modify the adjustment according to an expected counteraction that the adapted suspension assembly will have on the expected effect.

14. The system of claim 13 wherein:
the controller is further configured to monitor an effectiveness of the adaptation of the suspension assembly in counteracting the expected effect; and
upon a condition of a subsequent upcoming road segment similar to the detected condition being detected by the vision detector, the controller is further configured to modify the adaptation based on the monitored effectiveness and adapt the suspension assembly according to the modified adaptation such that the suspension assembly is adapted according to the modified adaptation as the vehicle drives over the subsequent upcoming road segment.

15. The system of claim 13 wherein:
the controller is further configured to determine the adjustment to the biometric monitor using artificial intelligence.

16. The system of claim 15 wherein:
the controller is further configured to determine the adaptation to the suspension assembly using artificial intelligence.

17. The system of claim 10 wherein:
the occupant of the vehicle is seated in a vehicle seat of the vehicle with the biometric monitor directed towards the vehicle seat.

18. A system for a vehicle having a vision detector configured to detect a condition of an upcoming road segment that the vehicle will be driving over, the system comprising:
a biometric monitor configured to monitor an occupant of the vehicle; and
a controller in communication with the biometric monitor and the vision detector, the controller configured to adjust the biometric monitor so that in monitoring the occupant of the vehicle as the vehicle drives over the upcoming road segment the biometric monitor is adjusted to counteract an expected effect that an anticipated jostling motion of the vehicle, based on the condition of the upcoming road segment, will have on the biometric monitor in monitoring the occupant of the vehicle when the vehicle drives over the upcoming road segment.

19. The system of claim 18 wherein:
the biometric monitor is configured to monitor the occupant of the vehicle by being configured to wirelessly monitor physical characteristics of the occupant of the vehicle.

20. The system of claim 18 wherein:
the controller is configured to adjust the biometric monitor by being configured to adjust a setting of the biometric monitor.

* * * * *